United States Patent [19]

Schuster et al.

[11] Patent Number: 5,057,151

[45] Date of Patent: Oct. 15, 1991

[54] PROCESS FOR PREPARING HYDROPHOBIC PARTICULATE SOLIDS CONTAINING SI-OH GROUPS AND A PROCESS FOR USING THE SAME

[75] Inventors: Johann Schuster; Horst Müller, both of Emmerting; Helmut Vorbuchner, Burghausen; Anton Maier, Burghausen; Ferdinand Pradl, Burghausen, all of Fed. Rep. of Germany

[73] Assignee: Wacker-Chemie GmbH, Munich, Fed. Rep. of Germany

[21] Appl. No.: 440,831

[22] Filed: Nov. 24, 1989

[30] Foreign Application Priority Data

Nov. 25, 1988 [DE] Fed. Rep. of Germany ....... 3839900

[51] Int. Cl.$^5$ ................................................ C09K 3/18
[52] U.S. Cl. .................................. 106/2; 106/287.12; 106/287.15; 523/212; 523/213; 428/405; 427/219
[58] Field of Search ................... 106/2, 287.12, 287.15; 523/212, 213; 428/405; 427/219

[56] References Cited

U.S. PATENT DOCUMENTS

| | | | |
|---|---|---|---|
| 3,868,345 | 2/1975 | Kratel et al. ........................ | 524/863 |
| 3,873,337 | 3/1975 | Läufer et al. ........................ | 106/481 |
| 3,953,487 | 4/1976 | Kratel et al. ........................ | 556/453 |
| 4,191,587 | 3/1980 | Kratel et al. ........................ | 106/490 |
| 4,208,316 | 6/1980 | Nauroth et al. ..................... | 106/490 |
| 4,209,432 | 6/1980 | Roth ................................. | 106/287.12 |
| 4,247,708 | 1/1981 | Tsutsumi et al. ................... | 106/490 |
| 4,273,589 | 6/1981 | Nauroth et al. ..................... | 106/484 |
| 4,308,074 | 12/1981 | Nauroth et al. ..................... | 106/466 |
| 4,344,800 | 8/1982 | Lutz .................................. | 106/490 |
| 4,849,022 | 7/1989 | Kobayashi et al. .................. | 106/490 |

FOREIGN PATENT DOCUMENTS

| | | |
|---|---|---|
| 326810 | 1/1989 | European Pat. Off. . |
| 2728490 | 6/1977 | Fed. Rep. of Germany . |
| 1157863 | 8/1958 | France . |
| 783868 | 10/1955 | United Kingdom . |
| 2056995 | 6/1980 | United Kingdom . |

OTHER PUBLICATIONS

Dialog Abstract of DE 2,728,490.

Primary Examiner—William R. Dixon, Jr.
Assistant Examiner—Helene Klemanski

[57] ABSTRACT

The invention relates to a process for rendering particulate solids containing Si-OH groups hydrophobic which comprises reacting a water repellent containing an organo-silicon compound with particulate solids containing Si-OH groups with simultaneous mechanical loading of the reaction mixture, in which from 5 to 50 percent by weight of the particulate solids containing Si-OH groups are used, based on the total weight of the reaction mixture containing particulate solids and water repellent, and the use of the resultant hydrophobic particulate solids in compositions containing diorganopolysiloxanes, which can be cured to form elastomers.

9 Claims, 1 Drawing Sheet

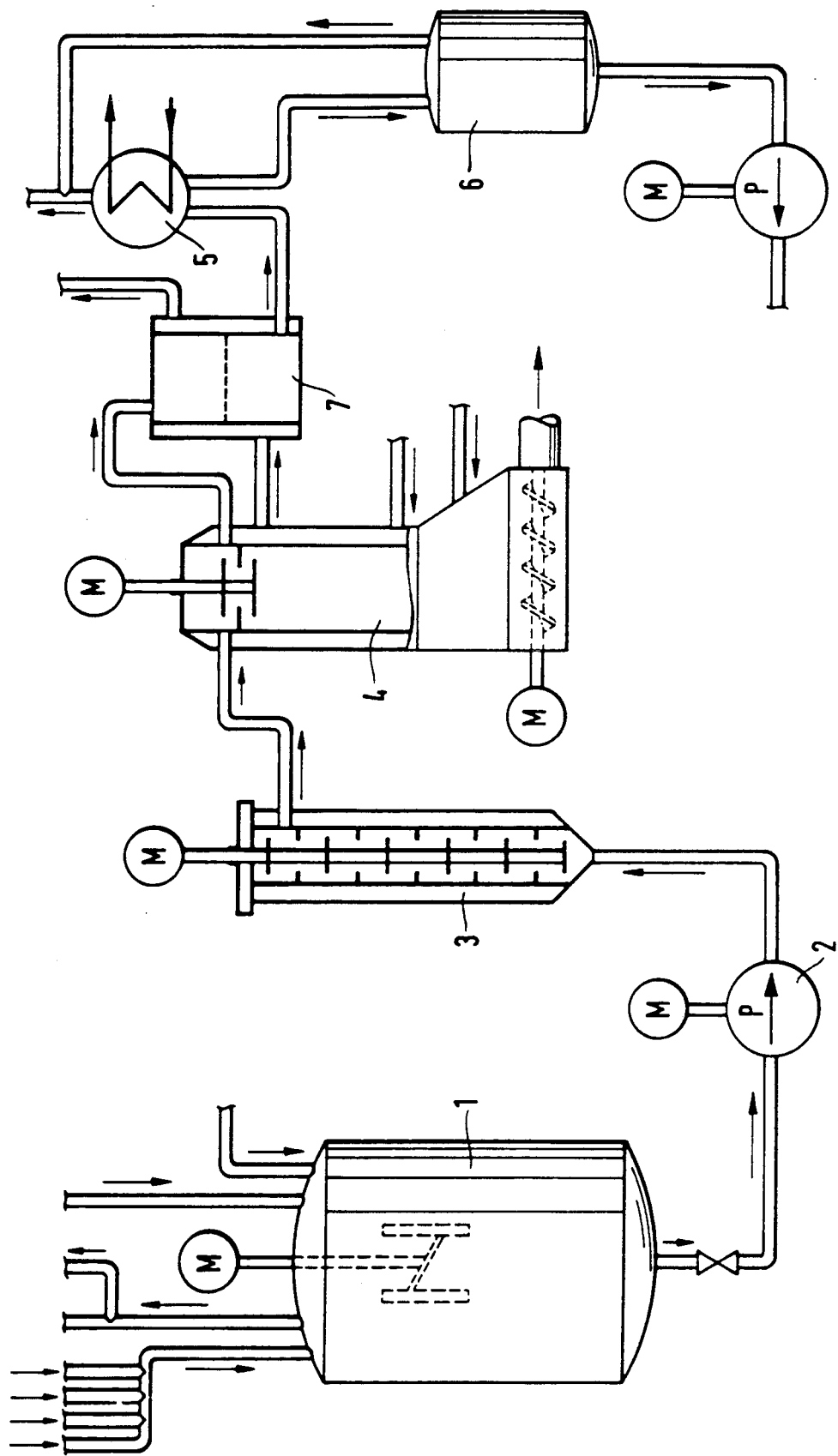

PROCESS FOR PREPARING HYDROPHOBIC PARTICULATE SOLIDS CONTAINING SI-OH GROUPS AND A PROCESS FOR USING THE SAME

A process for preparing hydrophobic particulate solids containing Si-OH groups and the use of the resultant hydrophobic particulate solids in compositions containing diorganopolysiloxanes, which can be cured to form elastomers.

BACKGROUND OF THE INVENTION

The invention relates to a process for preparing hydrophobic particulate solids containing Si-OH groups and to the use of the resultant hydrophobic particulate solids in compositions containing diorganopolysiloxanes, which can be cured to form elastomers.

U.S. Pat. No. 3,953,487 to Kratel and corresponding DE-OS 2,344,388 discloses that silicon dioxide can be rendered hydrophobic in inert, organic solvents and in a high speed homogenizing and dispersing apparatus driven at over 2000 revolutions per minute. However, at these high rotational speeds, high material wear and tear and abrasion result. Furthermore, 3 to 25 percent by weight of water repellent, based on the solids, are used in this process for rendering solids hydrophobic, which results in long reaction times, a relatively high expenditure of energy and poor production.

According to the prior art, compositions based on diorganopolysiloxanes, which are curable to form elastomers, and containing hydrophobic fillers, are prepared by rendering the filler hydrophobic by the addition of a water repellent during mixing of the filler with the diorganopolysiloxane, i.e. in situ. The use of a hydrophobic filler, which has been rendered hydrophobic in a fluidized bed, pug mill machine or stirred ball mill, etc. such as disclosed in U.S. Pat. No. 3,868,345 to Kratel, or in corresponding DE-OS 2,211,377 in compositions which are curable to form elastomers, is impossible in many cases, since the properties of the products prepared therefrom differ from those of the products produced in the in-situ process. However, the in-situ process has the disadvantages of a long batch cycle time and high emissions which occur in many places and are therefore difficult to control. Moreover, a selective control of the process for rendering fillers hydrophobic is scarcely possible and also, corrections to the filler content of the compositions based on diorganopolysiloxanes, which are curable to form elastomers are no longer possible since suitable fillers are not available.

Therefore, it is an object of the present invention to provide a process for rendering a particulate solid containing Si-OH groups hydrophobic. Another object of the present invention is to provide a process for rendering a particulate solid containing Si-OH groups hydrophobic and to selectively control the degree of water repellency. Still another object of the present invention is to provide a process for rendering a particulate solid containing Si-OH groups hydrophobic having a high and/or uniform degree of water repellency. A further object of the present invention is to provide a process for rendering a particulate solid containing Si-OH groups hydrophobic which may be used in preparing diorganopolysiloxanes which can be cured to form elastomers.

SUMMARY OF THE INVENTION

The foregoing objects and others which will become apparent from the following description are accomplished in accordance with this invention, generally speaking, by providing a process for rendering a particulate solid containing Si-OH groups hydrophobic which comprises reacting a water repellent containing organosilicon compounds with the particulate solid containing Si-OH groups with simultaneous mechanical loading of the reaction mixture, in which from 5 to 50 percent by weight of the particulate solid containing Si-OH groups, based on the total weight of the reaction mixture comprising particulate solid and water repellent, are used.

The invention further relates to a process for preparing compositions, which are curable to form elastomers containing diorganopolysiloxanes and a hydrophobic filler, in which at least a part of the filler is obtained by reacting a water repellent containing an organosilicon compound with a particulate solid containing Si-OH groups with simultaneous mechanical loading of the reaction mixture, wherein from 5 to 50 percent by weight of the particulate solid containing Si-OH groups, based on the total weight of the reaction mixture containing a particulate solid and water repellent, are used.

DESCRIPTION OF THE INVENTION

When a separate process is used for rendering the particulate solid hydrophobic, it is possible to selectively control the degree to which water repellency is imparted and to vary this within wide limits. Also, it is possible to impart high and/or uniform degrees of water repellency which is a prerequisite for many applications. In particular, this should be achieved without acidic or alkaline residues remaining in the particulate solid. Neither should neutral salts or other additives, which are not organosilicon compounds, remain in the solid. Therefore, the process of this invention allows a particulate solid to be rendered hydrophobic in such a manner that compositions which are curable to form elastomers containing diorganopolysiloxanes and solids which heretofore were prepared by the in-situ process, can now be produced by simply mixing the particulate solid which has been rendered hydrophobic, with the diorgano-polysiloxane. The use of a particulate solid which has previously been rendered hydrophobic significantly increases the capacity of the mixers. Emissions are confined to a central plant and are thereby easier to control. The consumption of water repellent can be significantly reduced in comparison with the in-situ process. The solids content of the compositions can subsequently be corrected easily by adding additional solids according to this invention. In the preparation of liquid rubber, [lacuna] notch-tough one- and two-component silicone rubber compositions which are crosslinkable by addition or condensation, only the solids prepared according to this invention are suitable. Only when these are used, can good flow characteristics, good transparency and low volatility, depending on the product, be achieved.

The process of this invention is carried out under simultaneous mechanical loading of the reaction mixture preferably in a mixer at rotational speeds of preferably 300 to 2000 revolutions per minute, particularly 300 to 1500 revolutions per minute.

Examples of mixers which may be employed are the Turrax mixer, the high speed mixer, the Henschel mixer and the turbine mixer. The process of this invention is preferably carried out in an inert atmosphere, the oxygen content being reduced to a maximum of 3 percent by volume. It is preferable to operate in an atmosphere of nitrogen or argon.

After the solid has been rendered hydrophobic, the excess water repellent is removed and is preferably used afresh with the next batch. Reacted water repellent and losses are replaced.

The degree to which the resultant hydrophobic particulate solid is rendered hydrophobic can easily be varied by varying the rotational speed of the mixer or the residence time. Preferred residence times are 10 to 1800 seconds.

The process can be carried out continuously or semicontinuously.

From 5 to 50 percent by weight, preferably from 20 to 30 percent by weight, of the particulate solid containing Si-OH groups are used, based on the total weight of the reaction mixture comprising particulate solid and water repellent. The proportions of ingredients in the process of this invention are, however, always designed such that the reaction mixture containing particulate solid and water repellent, has a paste-like consistency. It is possible, by virtue of this paste-like consistency, to expose the reaction mixture to high shear forces even at low rotational speeds of the mixer. These high shear forces lead to high mechanical loading of the reaction mixture, whereby agglomerates of the particulate solid are comminuted, which again brings about an increase in the water repellency.

The particulate solid containing Si-OH groups preferably has a BET surface area of 5 $m^2/g$ to 600 $m^2/g$, and more preferably from 150 $m^2/g$ to 300 $m^2/g$. Examples of particulate solids are quartz powders, diatomaceous earth, and clay minerals. Pyrogenically produced or precipitated silicon dioxide is preferably used.

The same water repellents containing organosilicon compounds can be used in this invention as have been used heretofore for rendering particulate solids containing Si-OH groups hydrophobic. These water repellents preferably contain from 1 to 5 percent by weight of water, based on the total weight of the water repellent. It is possible to have a higher water content, for example up to 20 percent by weight.

Instead of water, but preferably together with water, it is possible, if desired, to concomitantly use catalysts which are known per se to promote the reaction of finely divided-particle solids containing Si-OH groups with organosilicon compounds. Examples of suitable catalysts are hydrogen chloride, amines, for example n-butylamine and/or compounds of metals, for example titanium tetrachloride or dibutyltin dilaurate.

Preferred organosilicon compounds which may be used as water repellents are those of the general formula $$(R_3Si)_aZ$$

in which R represents the same or different monovalent hydrocarbon radicals or substituted monovalent hydrocarbon radicals, Z is halogen, hydrogen or a radical of the formula —OH, —OR', —NR'X, —ONR'$_2$, —OOCR', —O— or —N(X)—, where R' is an alkyl radical having from 1 to 4 carbon atoms and X is hydrogen or is the same as R', and a is 1 or 2. The most important example of a hydrocarbon radical represented by R is the methyl radical. Other examples of hydrocarbon radicals represented by R are octadecyl radicals, and the phenyl or vinyl radicals.

Examples of substituted hydrocarbon radicals represented by R are in particular, halogenated hydrocarbon radicals such as the 3,3,3-trifluoropropyl radical.

Examples of radicals represented by R' are the methyl, ethyl and propyl radical.

Examples of organosilicon compounds having the above formula are hexamethyldisilazane, trimethylsilanol, trimethylchlorosilane, trimethylethoxysilane, triorganosilyloxyacylates, such as vinyldimethylacetoxysilane, triorganosilylamines, such as trimethylsilylisopropylamine, trimethylsilylethylamine, dimethylphenylsilylpropylamine and vinyldimethylsilylbutylamine, triorganosilylaminooxy compounds, such as diethylaminooxytrimethylsilane and diethylaminooxydimethylphenylsilane, and additionally hexamethyldisiloxane, 1,3-divinyltetramethyldisiloxane, 1,3-diphenyltetramethyldisiloxane and 1,3-diphenyltetramethyldisilazane.

Other examples of organosilicon compounds are dimethyldichlorosilane, dimethyldiethoxysilane, dimethyldimethoxysilane, diphenyldiethoxysilane, vinylmethyldimethoxysilane, methyltriethoxysilane, octamethylcyclotetrasiloxane and/or dimethylpolysiloxanes having from 2 to 12 siloxane units per molecule and containing a hydroxyl group bonded to Si in each of the terminal units.

It is also possible to react mixtures of various organosilicon compounds with the particulate solid containing Si-OH groups.

Particularly good results are obtained when water repellents are used which contain from 70 to 89 percent by weight of hexamethyldisiloxane and/or trimethylsilanol, 10 to 30 percent by weight of hexamethyldisilazane and/or divinyltetramethyldisilazane and 1 to 5 percent by weight of water. The percent by weight is based on the total weight of water repellent.

The mixers are not generally equipped with heating devices or with devices for providing a pressure differential from the surrounding atmosphere. The process for rendering the solid hydrophobic is therefore preferably carried out without additional heating and at the pressure of the surrounding atmosphere, i.e. 1080 hPa (abs.) or about 1080 hPa (abs.). However, in the process of rendering the solid hydrophobic, it is possible and often desired, that temperatures up to the boiling point of the water repellent and/or other pressures, preferably in the range of from 1000 to 10,000 hPa (abs.) be used.

The hydrophobic particulate solid obtained from the process of this invention has a high bulk density without an additional densification step, which is advantageous for subsequent processing. The higher bulk density in comparison with the starting material results from the breakdown of voluminous agglomerates.

The design illustrated in the figure has proved to be particularly satisfactory in the continuous process for rendering hydrophobic a particulate solid containing Si-OH groups. The numbers in the figure represent the following components:

1-mixing vessel
2-pump
3-mixing chamber with rotor
4-drying equipment
5-condenser
6-buffer tank 7-heated dust filter All diorganopolysiloxanes which have been used or could have been used heretofore for compositions which cure or can be cured at room temperature or at an elevated temperature, can be used as diorganopolysiloxanes in the process of this invention for the preparation of compositions which can be cured to form elastomers containing diorgano-polysiloxanes and solids. The diorganopolysiloxanes can for example be represented by the general formula $$Z^1{}_n Si(R^1)O_{3-n}[Si(R^1{}_2)O]_x Si(R^1)_{3-n} Z^1{}_n$$

in which $R^1$ represents the same or different monovalent hydrocarbon radicals, substituted monovalent hydrocarbon radicals, and/or polymeric hydrocarbon radicals, and $Z^1$ represents a hydroxyl group, a hydrolyzable group and/or hydrolyzable atom, or in the case of compositions whose curing is initiated at elevated temperature by peroxides, $Z^1$ may also represent an alkyl radical, n has a value of 1, 2 or 3 and x represents an integer of at least 1.

Other siloxane units, which mostly occur only as impurities may be present within or along the siloxane chain in the formula represented above. However, these units are generally not shown in formulas of this type, and generally contain in addition to the diorganosiloxane units, siloxane units of the formulas $R^1SiO_{3/2}$, $R^1{}_3SiO_{1/2}$ and $SiO_{4/2}$, in which $R^1$ is the same as above. The amount of these other siloxane units should not exceed about 10 mole per cent.

In addition to the siloxane molecules in the chain, the diorganopolysiloxanes used may also contain up to 20 percent by weight of cyclic siloxane units of the formula $(R^1{}_2Si—O)_x$, in which $R^1$ and x are the same as above.

Examples of hydrocarbon radicals represented by $R^1$ are alkyl radicals, such as methyl, ethyl, propyl, butyl, hexyl and octyl radicals; alkenyl radicals such as the vinyl, allyl, ethylallyl and butadienyl radicals; and aryl radicals such as the phenyl and tolyl radicals.

Examples of substituted hydrocarbon radicals represented by $R^1$ are in particular halogenated hydrocarbon radicals such as the 3,3,3-trifluoropropyl radical, chlorophenyl and bromotolyl radicals; and cyanoalkyl radicals, such as the beta-cyanoethyl radical.

Examples of polymeric (which may also be termed "modifying") substituted and unsubstituted hydrocarbon radicals represented by $R^1$ are polystyryl radicals, polyvinyl acetate radicals, polyacrylate radicals, polymethacrylate radicals and polyacrylonitrile radicals bonded to silicon via carbon.

At least the predominant part of the radicals represented by $R^1$ preferably contains methyl groups, because of their availability. The other radicals represented by $R^1$ which may be present, if desired, are in particular vinyl groups and/or phenyl groups.

Where the compositions are stored in the absence of water, and which cure at room temperature when exposed to water to form elastomers, $Z^1$ usually represents hydrolyzable groups. Examples of groups of this type are amino, amido, aminoxy, oxime, alkoxy, alkoxyalkoxy (for example $CH_3OCH_2CH_2O$—), alkenyloxy (for example $H_2C═(CH_3)CO$—), acyloxy and phosphate groups. In particular, $Z^1$ preferably represents acyloxy groups due to their availability, particularly acetoxy groups. However, excellent results are also achieved when $Z^1$ represents for example oxime groups such as those of the formula $ON═C(CH_3)(C_2H_5)$.

Examples of hydrolyzable atoms represented by $Z^1$ are halogen and hydrogen atoms.

Examples of alkenyl groups are in particular vinyl groups.

The viscosity of the diorganopolysiloxanes used within the scope of the invention are preferably between 20 mPa·s and 50,000,000 mPa·s (25° C.), depending on the end product. Accordingly, the value of x is preferably from 15 to 5000.

Mixtures of various diorganopolysiloxanes may also be used.

Compositions which can be cured to form elastomers are prepared from the hydrophobic particulate solids produced according to this invention by mixing the hydrophobic solids with diorganopolysiloxanes and optionally with other substances at room temperature or only at slightly elevated temperatures, optionally after adding crosslinking agents. This mixing can be carried out in any desired known manner, for example in mechanical mixers.

Preferably at least 10 percent by weight, particularly 30 to 100 percent by weight of the hydrophobic particulate fillers produced according to this invention are used, based on the total weight of filler used.

Preferably, the fillers are used in amounts of at least 5 percent by weight, particularly from 5 to 50 percent by weight, based on the total weight of the composition which can be cured to form an elastomer.

If those with hydroxyl groups bonded to Si are the only reactive terminal units present in the diorganopolysiloxanes containing reactive terminal units, these diorgano-polysiloxanes must be reacted with crosslinking agents in a known manner, optionally in the presence of a condensation catalyst, in order to cure the diorganopolysiloxanes or to convert them into compounds which cure to form elastomers by exposure to water contained in the air, or optionally with the addition of additional water.

Examples of crosslinking agents of this type are in particular silanes of the general formula $$R^1{}_{4-t}SiZ^{1'}{}_t,$$

in which $R^1$ is the same as above, $Z^{1'}$ is a hydrolyzable group and/or a hydrolyzable atom and t is 3 or 4. The groups and atoms listed above for $Z^1$ are also applicable in their entirety for the hydrolyzable groups $Z^{1'}$ and the hydrolyzable atoms $Z^{1'}$.

Examples of silanes of the formula given above are methyltriacetoxysilane, isopropyltriacetoxysilane, isopropoxytriacetoxysilane, vinyltriacetoxysilane, methyltrisdiethylaminoxysilane, methyltris(cyclohexylamino)silane, methyltris(diethylphosphato)silane and methyltris(methyl-ethylketoximo)silane.

Moreover, instead of the silanes, or as a mixture with silanes of the above formula, it is also possible for example to use polysiloxanes which contain at least three (3) groups or atoms per molecule, where the silicon valencies which are not saturated by $Z^{1'}$ groups or atoms are saturated by siloxane oxygen atoms and optionally $R^1$ groups. The best known examples of crosslinking agents of the latter type are polyethyl silicate having a $SiO_2$ content of about 40 percent by weight, hexamethoxydisiloxane and methylhydrogenpolysiloxanes.

Examples of well known condensation catalysts are tin salts of fatty acids, such as dibutyltin dilaurate, dibutyltin diacetate and tin(II) octoate.

Where the only reactive terminal units present in the diorganopolysiloxanes are alkenyl groups, the curing of the compositions to form elastomers may be carried out with organopolysiloxanes which contain on average of at least three (3) hydrogen atoms bonded to Si per molecule, such as methylhydrogenpolysiloxane, in the presence of catalysts which promote the addition of alkenyl groups to Si-bonded hydrogen atoms, such as hexachloroplatinic acid or Pt complexes.

Finally, peroxides may be used to cure diorganopolysiloxane compositions to form elastomers. Here, the peroxides bring about free-radical crosslinking of alkyl groups and alkenyl groups which is initiated at elevated temperatures. Examples of peroxides which may be used are dibenzoyl peroxide, dicumyl peroxide, m-Cl-benzoyl peroxide or 2,4-dichlorobenzoyl peroxide.

The compositions which can be cured to form elastomers may optionally contain other substances which have been used heretofore, in addition to the diorganopolysiloxanes, the fillers of this invention, crosslinking agents and crosslinking catalysts. Examples of additional substances which may be employed are fillers which have not been rendered hydrophobic having a surface area of less than 50 $m^2/g$, such as quartz powder, diatomaceous earth, so-called molecular sieves, such as sodium calcium aluminum silicate, or zirconium silicate and calcium carbonate, or additionally pyrogenically produced silicon dioxide which has not been rendered hydrophobic, organic resins, such as polyvinyl chloride powder, organopolysiloxane resins, fibrous fillers, such as asbestos, glass fibers, carbon fibers and organic fibers, pigments, soluble dyes, odorants, corrosion inhibitors, agents which stabilize the compositions against the effect of water, such as acetic anhydride, agents which delay curing, such as ethinylcyclohexanol and plasticizers, such as dimethylpolysiloxanes which have been terminally blocked with trimethylsiloxy groups.

The following examples are intended to illustrate the invention, but not limit the invention.

EXAMPLE 1

About 1.3 liters of a mixture containing 60 percent by weight of trimethylsilanol and 40 percent by weight of hexamethyldisiloxane were placed in a 5 liter apparatus equipped with a stirrer. The apparatus was rendered inert with nitrogen and then 450 g of pyrogenic silicon dioxide having a surface area of 300 $m^2/g$ were admixed with stirring at 300 rpm (revolutions per minute). About 64 g of hexamethyldisilazane and 7 g of water were then added. The paste was mixed using a high speed mixer at 1000 rpm for 1 hour, with gentle nitrogen purging. During this procedure, the temperature rose to 70° C. The volatile constituents were then distilled off, initially at normal pressure and then under vacuum and the silicon dioxide was dried at 200° C. to constant weight. Subsequent analysis gave a carbon content of 4.7 percent by weight.

EXAMPLE 2

About 5 kg of highly dispersed silica having a BET surface area of 300 $m^2/g$ and 30 kg of a mixture, containing 60 percent by weight of trimethylsilanol and 40 percent by weight of hexamethyldisiloxane were placed in a closed 75 liter high speed mixer fitted with a stripping device. After rendering the equipment inert with nitrogen, 2.3 kg of hexamethyldisilazane and 0.8 kg of water were added with stirring (200 rpm). Then, an additional 7 kg of the above mentioned silica was metered in using a membrane pump. The paste arising by this procedure was then mixed at 800 rpm for 10 minutes. The excess of water repellent was then distilled off. The solid obtained in this way had a carbon content of 4.8 percent.

EXAMPLE 3

About 50 kg/h of fine-particle silica having a BET surface area of 300 $m^2/g$ and 170 kg/h of a water repellent mixture, containing 154 kg of a mixture of 60 percent by 5 weight of trimethylsilanol, 40 percent by weight of hexamethyldisiloxane and 12 kg of hexamethyldisilazane and 4.0 kg of water were fed into mixing vessel (1). During this procedure, mixing vessel (1) was rendered inert with nitrogen. The paste forming in the mixing vessel was pumped by means of a pump (2) through a mixing chamber (3) in which the paste was intensively sheared by a rotor running at 800 rpm. Here, the flow through the mixing chamber was in the upward direction. The overflow ran into drying equipment (4), in which the excess of water repellent was removed from the solid by means of evaporation. The drying equipment was also rendered inert with nitrogen. The evaporated excess water repellent was transferred to intermediate storage in a buffer tank (6) via a heated dust filter (7) and a condenser (5).

EXAMPLE 4

About 20 kg of quartz powder (Sicron 3000, supplied by Quarzwerke Frechen) and 30 kg of a mixture, containing 60 percent by weight of trimethylsilanol and 40 percent by weight of hexamethyldisiloxane were placed in a closed 75 liter high speed mixer fitted with a stripping device, the equipment was rendered inert with nitrogen and then 2.3 kg of hexamethyldisilazane and 0.8 liter of water were added. The mixture was stirred at 800 rpm for 5 minutes. After distilling off the excess water repellent, a hydrophobic quartz powder was obtained.

EXAMPLE 5 AND COMPARISON EXAMPLE

A base composition for compositions which crosslink by addition, was prepared in the following manner:

About 500 g of a dimethylpolysiloxane having vinyl terminal groups and having a viscosity of 20,000 mPa·s (25° C.) were placed in a 5 liter laboratory kneader, heated to 150° C., and mixed with 390 g of a filler. A very stiff composition resulted, which was then diluted with 410 g of the dimethylpolysiloxane mentioned above. Volatile constituents were removed by kneading in vacuo (10 mbar) at 150° C. for one hour. An "A" and a "B" component were then prepared in a planetary mixer from this base composition. The "A" component which was mixed for 30 minutes at room temperature and normal pressure, contained the base composition and 100 ppm of hexachloroplatinic acid. The "B" component, which was also mixed for 30 minutes at room temperature and normal pressure, contained 95 percent by weight of base composition and 4 percent by weight of a siloxane crosslinking agent having 0.18 mol percent of Si-H, and 1 percent by weight of divinyltetramethyldisiloxane.

Components "A" and "B" were mixed in a ratio of 1:1 and vulcanized at temperatures above 100° C. Vulcanizates were obtained having the following properties:

| Example | Filler | Viscosity of the "B" component (Pa · s) | Heat test (%) | Transparency |
|---|---|---|---|---|
| 5 | According to Example 2 | 900 | 11 | very good |
| Comparison | According to DE-OS 2,211,377 | 3500 | 113 | poor |
| Specified values in accordance with product specification | | 700–1000 | <50 | very good |

EXAMPLE 6

A base composition for compositions which crosslink by condensation was prepared in the following manner:

About 2400 g of a dimethylpolysiloxane having OH terminal groups and having a viscosity of 6000 mPa·s (25° C.) were placed in a 10 liter laboratory kneader and 2400 g of the filler prepared according to Example 1 were added. After the addition of filler had been completed, kneading was carried out for 1 hour. The composition was then baked for 3 hours at 150° C. in vacuo and subsequently diluted with 600 g of the dimethylpolysiloxane mentioned above and 1200 g of a dimethylpolysiloxane endblocked with trimethylsilyl groups, and having a viscosity of 100 mPa·s (25° C.).

EXAMPLE 7

A base composition for dental impression materials was prepared in the following manner:

About 490 g of a dimethylpolysiloxane having vinyl terminal groups and having a viscosity of 20,000 mPa·s (25° C.) were placed in a 5 liter laboratory kneader and a total of 920 g of filler prepared according to Example 4 was added. After kneading for one hour, the composition was diluted with 125 g of the dimethylpolysiloxane mentioned above. Dental impression materials having a long shelf life were prepared from this base composition.

What is claimed is:

1. A process for rendering a particulate solid containing Si-OH groups hydrophobic which comprises reacting a water repellent containing an organosilicon compound with the particulate solid containing Si-OH groups with simultaneous mechanical loading of the reaction mixture, in which from 5 to 50 percent by weight of the particulate solid containing Si-OH groups are used, based on the total weight of the reaction mixture containing particulate solid and water repellent, and wherein the water repellent contains from 1 to 5 percent by weight of water based on the weight of the water repellent.

2. The process of claim 1, wherein the reaction is carried out in an inert atmosphere and the oxygen content is reduced to a maximum of 3 percent by volume.

3. The process of claim 1, wherein from 20 to 30 percent by weight of the particulate solid containing Si-OH groups are used, based on the total weight of the reaction mixture containing particulate solid and water repellent.

4. The process of claim 2, wherein from 20 to 30 percent by weight of the particulate solid containing Si-OH groups are used, based on the total weight of the particulate solid and water repellent.

5. The process of claim 1, wherein the water repellent comprises from 70 to 89 percent by weight of an organosilicon compound selected from the group consisting of hexamethyldisiloxane, trimethylsilanol and mixtures thereof, from 10 to 30 percent by weight of an organosilicon compound selected from the group consisting of hexamethyldisilazane, divinyltetramethyldisilazane and mixtures thereof, and from 1 to 5 percent by weight of water, where the percent by weight is based on the total weight of the water repellent.

6. The process of claim 2, wherein the water repellent comprises from 70 to 89 percent by weight of an organosilicon compound selected from the group consisting of hexamethyldisiloxane, trimethylsilanol and mixtures thereof, from 10 to 30 percent by weight of an organosilicon compound selected from the group consisting of hexamethyldisilazane, divinyltetramethyldisilazane and mixtures thereof, and from 1 to 5 percent by weight of water, where the percent by weight is based on the total weight of the water repellent.

7. The process of claim 3, wherein the water repellent comprises from 70 to 89 percent by weight of an organosilicon compound selected from the group consisting of hexamethyldisiloxane, trimethylsilanol and mixtures thereof, from 10 to 30 percent by weight of an organosilicon compound selected from the group consisting of hexamethyldisilazane, divinyltetramethyldisilazane and mixtures thereof, and from 1 to 5 percent by weight of water, where the percent by weight is based on the total weight of the water repellent.

8. The process of claim 4, wherein the water repellent comprises from 70 to 89 percent by weight of an organosilicon compound selected from the group consisting of hexamethyldisiloxane, trimethylsilanol and mixtures thereof, from 10 to 30 percent by weight of an organosilicon compound selected from the group consisting of hexamethyldisilazane, divinlytetramethyldisilazane and mixtures thereof, and from 1 to 5 percent by weight of water, where the percent by weight is based on the total weight of the water repellent.

9. A composition containing diorganopolysiloxanes which are curable to form elastomers, and a particulate solid in which at least a part of the particulate solid is obtained by reacting the particulate solid having Si-OH groups with a water repellent containing an organosilicon compound with simultaneous mechanical loading of the reaction mixture, in which from 5 to 50 percent by weight of the particulate solid are used, based on the weight of the reaction mixture containing particulate solid and water repellent, and wherein the water repellent contains from 1 to 5 percent by weight of water based on the weight of the water repellent.

* * * * *